US006313382B1

(12) United States Patent
Fox et al.

(10) Patent No.: US 6,313,382 B1
(45) Date of Patent: Nov. 6, 2001

(54) INBRED MAIZE LINE PH8V0

(75) Inventors: Russell L. Fox, Princeton, IL (US); Charles Thomas Cunnyngham, Tipton, IN (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/490,299

(22) Filed: Jan. 24, 2000

(51) Int. Cl.$^7$ ............................... A01H 5/00; A01H 4/00; A01H 1/00; C12X 5/04
(52) U.S. Cl. ....................... 800/320.1; 800/298; 800/275; 800/271; 800/268; 800/266; 800/301; 800/302; 800/303; 435/412; 435/424; 435/430; 435/430.1
(58) Field of Search ................................ 800/320.1, 298, 800/275, 271, 266, 268, 301–303; 435/412, 424, 430, 430.1

(56) References Cited

PUBLICATIONS

Conger, B.V., et al. (1987) "Somatic Embryogenesis From Cultured Leaf Segments of *Zea Mays*", *Plant Cell Reports*, 6:345–347.

Duncan, D.R., et al. (1985) "The Production of Callus Capable of Plant Regeneration From Immature Embryos of Numerous *Zea Mays* Genotypes", *Planta*, 165:322–332.

Edallo, et al. (1981) "Chromosomal Variation and Frequency of Spontaneous Mutation Associated with in Vitro Culture and Plant Regeneration in Maize", *Maydica*, XXVI: 39–56.

Green, et al., (1975) "Plant Regeneration From Tissue Cultures of Maize", *Crop Science*, vol. 15, pp. 417–421.

Green, C.E., et al. (1982) "Plant Regeneration in Tissue Cultures of Maize" *Maize for Biological Research*, pp. 367–372.

Hallauer, A.R. et al. (1988) "Corn Breeding" *Corn and Corn Improvement*, No. 18, pp. 463–481.

Meghji, M.R., et al. (1984). "Inbreeding Depression, Inbred & Hybrid Grain Yields, and Other Traits of Maize Genotypes Representing Three Eras", *Crop Science*, vol. 24, pp. 545–549.

Phillips, et al. (1988) "Cell/Tissue Culture and In Vitro Manipulation", *Corn & Corn Improvement*, 3rd Ed., ASA Publication, No. 18, pp. 345–387.

Poehlman et al., (1995) *Breeding Field Crop*, 4th Ed., Iowa State University Press, Ames, IA., pp. 132–155 and 321–344.

Rao, K.V., et al., (1986) "Somatic Embryogenesis in Glume Callus Cultures", *Maize Genetics Cooperative Newsletter*, No. 60, pp. 64–65.

Sass, John F. (1977) "Morphology", *Corn & Corn Improvement*, ASA Publication. Madison, Wisconsin, pp. 89–109.

Songstad, D.D. et al. (1988) "Effect of ACC (1–aminocyclopropane–1–carboxyclic acid), Silver Nitrate & Norbonadiene on Plant Regeneration From Maize Callus Cultures", *Plant Cell Reports*, 7:262–265.

Tomes, et al. (1985) "The Effect of Parental Genotype on Initiation of Embryogenic Callus From Elite Maize (*Zea Mays* L.) Germplasm", *Theor. Appl. Genet.*, vol. 70, p. 505–509.

Troyer, et al. (1985) "Selection for Early Flowering in Corn: 10 Late Synthetics", *Crop Science*, vol. 25, pp. 695–697.

Umbeck, et al. (1983) "Reversion of Male–Sterile T–Cytoplasm Maize to Male Fertility in Tissue Culture", *Crop Science*, vol. 23, pp. 584–588.

Wright, Harold (1980) "Commercial Hybrid Seed Production", *Hybridization of Crop Plants*, Ch. 8: 161–176.

Wych, Robert D. (1988) "Production of Hybrid Seed", *Corn and Corn Improvement*, Ch. 9, pp. 565–607.

Lee, Michael (1994) "Inbred Lines of Maize and Their Molecular Markers", *The Maize Handbook* Ch. 65:423–432.

Boppenmaier, et al., "Comparsons Among Strains of Inbreds for RFLPs", Maize Genetics Cooperative Newsletter, 65:1991, p. 90.

Smith, J.S.C., et al., "The Identification of Female Selfs in Hybrid Maize: A Comparison Using Electrophoresis and Morphology", Seed Science and Technology 14, 1–8.

*Primary Examiner*—Gary Benzion
(74) *Attorney, Agent, or Firm*—Pioneer Hi-Bred International, Inc.

(57) ABSTRACT

An inbred maize line, designated PH8V0, the plants and seeds of inbred maize line PH8V0, methods for producing a maize plant, either inbred or hybrid, produced by crossing the inbred maize line PH8V0 with itself or with another maize plant, and hybrid maize seeds and plants produced by crossing the inbred line PH8V0 with another maize line or plant and to methods for producing a maize plant containing in its genetic material one or more transgenes and to the transgenic maize plants produced by that method. This invention also relates to inbred maize lines derived from inbred maize line PH8V0, to methods for producing other inbred maize lines derived from inbred maize fine PH8V0 and to the inbred maize lines derived by the use of those methods.

49 Claims, No Drawings

INBRED MAIZE LINE PH8V0

FIELD OF THE INVENTION

This invention is in the field of maize breeding, specifically relating to an inbred maize line designated PH8V0.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (zea mays L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

A reliable method of controlling male fertility in plants offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two maize inbreds are planted in a field, and the pollen-bearing tassels are removed from one of the inbreds (female). Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile maize and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. Pat. No. 5,432,068, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. : 4,936,904). Application of the gametocide, timing of the application and genotype specificity often limit the usefulness of the approach.

Development of Maize Inbred Lines

The use of male sterile inbreds is but one factor in the production of maize hybrids. Plant breeding techniques known in the art and used in a maize plant breeding program include, but are not limited to, recurrent selection, backcrossing, pedigree breeding, restriction length polymorphism enhanced selection, genetic marker enhanced selection and transformation. The development of maize hybrids in a maize plant breeding program requires, in general, the development of homozygous inbred lines, the crossing of these lines, and the evaluation of the crosses. Pedigree breeding and recurrent selection breeding methods are used to develop inbred lines from breeding populations. Maize plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a maize plant breeding program, are expensive and time consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Recurrent selection breeding, backcrossing for example, can be used to improve an inbred line and a hybrid which is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a maize plant breeding program, elite inbreds can be used as a parental line or starting material or source population and can serve as either the donor or recurrent parent.

Development of Maize Hybrids

A single cross maize hybrid results from the cross of two inbred lines, each of which has a genotype that complements the genotype of the other. The hybrid progeny of the first generation is designated $F_1$. In the development of commercial hybrids in a maize plant breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in maize, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines (or synthetics) crossed in pairs (A×B and C×D) and then the two $F_1$ hybrids are crossed again (A×B) ×(C×D). A three-way cross hybrid is produced from three inbred lines (or synthetics) where two of the inbred lines (or synthetics) are crossed (A×B) and then the resulting $F_1$ hybrid is crossed with the third inbred (or synthetics) (A×B)×C. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self pollination. This inadvertently self pollinated seed may be unintentionally harvested and packaged with hybrid seed.

Once the seed is planted, it is possible to identify and select these self pollinated plants. These self pollinated plants will be genetically equivalent to the female inbred line used to produce the hybrid.

Typically these self pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1–8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29–42.

As is readily apparent to one skilled in the art, the foregoing are only some of the various ways by which the inbred can be obtained by those looking to use the germplasm. Other means are available, and the above examples are illustrative only.

Maize is an important and valuable field crop. Thus, a continuing goal of plant breeders is to develop high-yielding maize hybrids that are agronomically sound based on stable inbred lines. The reasons for this goal are obvious: to maximize the amount of grain produced with the inputs used and minimize susceptibility of the crop to pests and environmental stresses. To accomplish this goal, the maize breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. The probability of selecting any one individual with a specific genotype from a breeding cross is infinitesimal due to the large number of segregating genes and the unlimited recombinations of these genes, some of which may be closely linked. However, the genetic variation among individual progeny of a breeding cross allows for the identification of rare and valuable new genotypes. These new genotypes are neither predictable nor incremental in value, but rather the result of manifested genetic variation combined with selection methods, environments and the actions of the breeder.

Thus, even if the entire genotypes of the parents of the breeding cross were characterized and a desired genotype known, only a few if any individuals having the desired genotype may be found in a large segregating $F_2$ population. Typically, however, neither the genotypes of the breeding cross parents nor the desired genotype to be selected is known in any detail. In addition to the preceding problem, it is not known how the genotype would react with the environment. This genotype by environment interaction is an important, yet unpredictable, factor in plant breeding. A breeder of ordinary skill in the art cannot predict the genotype, how that genotype will interact with various climatic conditions or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new maize inbred line.

SUMMARY OF THE INVENTION

According to the invention, there is provided a novel inbred maize line, designated PH8V0. This invention thus relates to the seeds of inbred maize line PH8V0, to the plants of inbred maize line PH8V0, to methods for producing a maize plant produced by crossing the inbred maize line PH8V0 with itself or another maize line, and to methods for producing a maize plant containing in its genetic material one or more transgenes and to the transgenic maize plants produced by that method. This invention also relates to inbred maize lines derived from inbred maize line PH8V0, to methods for producing other inbred maize lines derived from inbred maize line PH8V0 and to the inbred maize lines derived by the use of those methods. This invention further relates to hybrid maize seeds and plants produced by crossing the inbred line PH8V0 with another maize line.

Definitions

In the description and examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. These designators will follow the descriptors to denote how the values are to be interpreted. Below are the descriptors used in the data tables included herein.

ANT ROT=ANTHRACNOSE STALK ROT (*Colletotrichum graminicola*). A 1 to 9 visual rating indicating the resistance to Anthracnose Stalk Rot. A higher score indicates a higher resistance.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Yield of the grain at harvest in bushels per acre adjusted to 15.5% moisture.

CLD TST=COLD TEST. The percent of plants that germinate under cold test conditions.

CLN=CORN LETHAL NECROSIS. Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance.

COM RST=COMMON RUST (*Puccinia sorghi*). A 1 to 9 visual rating indicating the resistance to Common Rust. A higher score indicates a higher resistance.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

DIP ERS=DIPLODIA EAR MOLD SCORES (*Diplodia maydis and Diplodia macrospora*). A 1 to 9 visual rating indicating the resistance to Diplodia Ear Mold. A higher score indicates a higher resistance.

DRP EAR=DROPPED EARS. A measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

EAR HT=EAR HEIGHT. The ear height is a measure from the ground to the highest placed developed ear node attachment and is measured in inches.

EAR MLD=General Ear Mold. Visual rating (1–9 score) where a "1" is very susceptible and a "9" is very resistant. This is based on overall rating for ear mold of mature ears without determining the specific mold organism, and may not be predictive for a specific ear mold.

EAR SZ=EAR SIZE. A 1 to 9 visual rating of ear size. The higher the rating the larger the ear size.

ECB 1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance.

ECB 2IT=EUROPEAN CORN BORER SECOND GENERATION INCHES OF TUNNELING (*Ostrinia nubilalis*). Average inches of tunneling per plant in the stalk.

ECB 2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECB DPE=EUROPEAN CORN BORER DROPPED EARS (*Ostrinia nubilalis*). Dropped ears due to European Corn Borer. Percentage of plants that did not drop ears under second generation corn borer infestation.

EGR WTH=EARLY GROWTH. This is a measure of the relative height and size of a corn seedling at the 2–4 leaf stage of growth. This is a visual rating (1 to 9), with 1 being weak or slow growth, 5 being average growth and 9 being strong growth. Taller plants, wider leaves, more green mass and darker color constitute higher score.

EST CNT=EARLY STAND COUNT. This is a measure of the stand establishment in the spring and represents the number of plants that emerge on per plot basis for the inbred or hybrid.

EYE SPT=Eye Spot (*Kabatiella zeae* or *Aureobasidium zeae*). A 1 to 9 visual rating indicating the resistance to Eye Spot. A higher score indicates a higher resistance.

FUS ERS=FUSARIUM EAR ROT SCORE (*Fusarium moniliforme* or *Fusarium subglutinans*). A 1 to 9 visual rating indicating the resistance to Fusarium ear rot. A higher score indicates a higher resistance.

GDU=Growing Degree Units. Using the Barger Heat Unit Theory, which assumes that maize growth occurs in the temperature range 50° F.–86° F. and that temperatures outside this range slow down growth; the maximum daily heat unit accumulation is 36 and the minimum daily heat unit accumulation is 0. The seasonal accumulation of GDU is a major factor in determining maturity zones.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GIB ERS=GIBBERELLA EAR ROT (PINK MOLD) (*Gibberella zeae*). A 1 to 9 visual rating indicating the resistance to Gibberella Ear Rot. A higher score indicates a higher resistance.

GLF SPT=Gray Leaf Spot (*Cercospora zeae-maydis*). A 1 to 9 visual rating indicating the resistance to Gray Leaf Spot. A higher score indicates a higher resistance.

GOS WLT=Goss' Wilt (*Corynebacterium nebraskense*). A 1 to 9 visual rating indicating the resistance to Goss' Wilt. A higher score indicates a higher resistance.

GRN APP=GRAIN APPEARANCE. This is a 1 to 9 rating for the general appearance of the shelled grain as it is harvested based on such factors as the color of harvested grain, any mold on the grain, and any cracked grain. High scores indicate good grain quality.

H/POP=YIELD AT HIGH DENSITY. Yield ability at relatively high plant densities on 1–9 relative rating system with a higher number indicating the hybrid responds well to high plant densities for yield relative to other hybrids. A 1, 5, and 9 would represent very poor, average, and very good yield response, respectively, to increased plant density.

HC BLT=HELMINTHOSPORIUM CARBONUM LEAF BLIGHT (*Helminthosporium carbonum*). A 1 to 9 visual rating indicating the resistance to Helminthosporium infection. A higher score indicates a higher resistance.

HD SMT=HEAD SMUT (*Sphacelotheca reiliana*). This score indicates the percentage of plants not infected.

HSK CVR=HUSK COVER. A 1 to 9 score based on performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE. GROSS INCOME advantage of variety #1 over variety #2.

KSZ DCD=KERNEL SIZE DISCARD. The percent of discard seed; calculated as the sum of discarded tip kernels and extra large kernels.

L/POP=YIELD AT LOW DENSITY. Yield ability at relatively low plant densities on a 1–9 relative system with a higher number indicating the hybrid responds well to low plant densities for yield relative to other hybrids. A 1, 5, and 9 would represent very poor, average, and very good yield response, respectively, to low plant density.

MDM CPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance.

MST=HARVEST MOISTURE. The moisture is the actual percentage moisture of the grain at harvest.

MST ADV=MOISTURE ADVANTAGE. The moisture advantage of variety #1 over variety #2 as calculated by: MOISTURE of variety #2—MOISTURE of variety #1=MOISTURE ADVANTAGE of variety #1.

NLF BLT=Northern Leaf Blight (*Helminthosporium turcicum* or *Exserohilum turcicum*). A 1 to 9 visual rating indicating the resistance to Northern Leaf Blight. A higher score indicates a higher resistance.

OILT=GRAIN OIL. Absolute value of oil content of the kernel as predicted by Near-Infrared Transmittance and expressed as a percent of dry matter.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

POP K/A=PLANT POPULATIONS. Measured as 1000s per acre.

POP ADV=PLANT POPULATION ADVANTAGE. The plant population advantage of variety #1 over variety #2 as calculated by PLANT POPULATION of variety #2—PLANT POPULATION of variety #1 =PLANT POPULATION ADVANTAGE of variety #1.

PRM=PREDICTED RELATIVE MATURITY. This trait, predicted relative maturity, is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PRM SHD=A relative measure of the growing degree units (GDU) required to reach 50% pollen shed. Relative values are predicted values from the linear regression of observed GDU's on relative maturity of commercial checks.

PROT=GRAIN PROTEIN. Absolute value of protein content of the kernel as predicted by Near-Infrared Transmittance and expressed as a percent of dry matter.

RT LDG=ROOT LODGING. Root lodging is the percentage of plants that do not root lodge; plants that lean from the vertical axis at an approximately 30° angle or greater would be counted as root lodged.

RTL ADV=ROOT LODGING ADVANTAGE. The root lodging advantage of variety #1 over variety #2.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SLF BLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SOU RST=SOUTHERN RUST (*Puccinia polysora*). A 1 to 9 visual rating indicating the resistance to Southern Rust. A higher score indicates a higher resistance.

STA GRN=STAY GREEN. Stay green is the measure of plant health near the time of black layer formation (physiological maturity). A high score indicates better late-season plant health.

STD ADV=STALK STANDING ADVANTAGE. The advantage of variety #1 over variety #2 for the trait STK CNT.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

STRT=GRAIN STARCH. Absolute value of starch content of the kernel as predicted by Near-infrared Transmittance and expressed as a percent of dry matter.

STW WLT=Stewart's Wilt (*Erwinia stewartii*). A 1 to 9 visual rating indicating the resistance to Stewart's Wilt. A higher score indicates a higher resistance.

TAS BLS=TASSEL BLAST. A 1 to 9 visual rating was used to measure the degree of blasting (necrosis due to heat stress) of the tassel at the time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data are given as a percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for 15.5 percent moisture.

TSW ADV=TEST WEIGHT ADVANTAGE. The test weight advantage of variety #1 over variety #2.

WIN M %=PERCENT MOISTURE WINS.

WIN Y %=PERCENT YIELD WINS.

YLD=YIELD. It is the same as BU ACR ABS.

YLD ADV=YIELD ADVANTAGE. The yield advantage of variety #1 over variety #2 as calculated by: YIELD of variety #1—YIELD variety #2 =yield advantage of variety #1.

YLD SC=YIELD SCORE. A 1 to 9 visual rating was used to give a relative rating for yield based on plot ear piles. The higher the rating the greater visual yield appearance.

DETAILED DESCRIPTION OF THE INVENTION

Inbred maize lines are typically developed for use in the production of hybrid maize lines. Inbred maize lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the maize plants to be examined. Phenotypic characteristics most often observed are for traits associated with plant morphology, ear and kernel morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The most widely used of these laboratory techniques are Isozyme Electrophoresis and RFLPs as discussed in Lee, M., "Inbred Lines of Maize and Their Molecular Markers," *The Maize Handbook*, (Springer-Verlag, New York, Inc. 1994, at 423–432) incorporated herein by reference.

Isozyme Electrophoresis is a useful tool in determining genetic composition, although it has relatively low number of available markers and the low number of allelic variants among maize inbreds. RFLPs have the advantage of revealing an exceptionally high degree of allelic variation in maize and the number of available markers is almost limitless.

Maize RFLP linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference. This study used 101 RFLP markers to analyze the patterns of 2 to 3 different deposits each of five different inbred lines. The inbred lines had been selfed from 9 to 12 times before being adopted into 2 to 3 different breeding programs. It was results from these 2 to 3 different breeding programs that supplied the different deposits for analysis. These five lines were maintained in the separate breeding programs by selfing or sibbing and rogueing off-type plants for an additional one to eight generations. After the RFLP analysis was completed, it was determined the five lines showed 0–2% residual heterozygosity. Although this was a relatively small study, it can be seen using RFLPs that the lines had been highly homozygous prior to the separate strain maintenance.

Inbred maize line PH8V0 is a yellow, dent maize inbred that is suited as a female for producing first generation F1 maize hybrids. Inbred maize line PH8V0 is best adapted to the Central Corn Belt region of the United States and can be used to produce hybrids from approximately 106 relative maturity based on the Comparative Relative Maturity Rating System for harvest moisture of grain. Inbred maize line PH8V0 demonstrates good yields, good cold test scores and waxy starch grain. In hybrid combination, including for its area of adaptation, inbred PH8V0 demonstrates high yield, good resistance to stalk lodging, good staygreen, low harvest moisture and below average plant height.

The inbred has shown uniformity and stability within the limits of environmental influence for all the traits as described in the Variety Description Information (Table 1) that follows. The inbred has been self-pollinated and ear-rowed a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in PH8V0.

Inbred maize line PH8V0, being substantially homozygous, can be reproduced by planting seeds of the line, growing the resulting maize plants under self-pollinating or sib-pollinating conditions with adequate isolation, and harvesting the resulting seed, using techniques familiar to the agricultural arts.

TABLE 1

VARIETY DESCRIPTION INFORMATION
VARIETY = PH8V0

1. TYPE: (describe intermediate types in Comments section):
  2   1 = Sweet 2 = Dent 3 = Flint 4 = Flour 5 = Pop 6 = Ornamental
2. MATURITY:

| DAYS | HEAT UNITS | | |
|---|---|---|---|
| 071 | 1,336.7 | From emergence to 50% of plants in silk | |
| 072 | 1,365.7 | From emergence to 50% of plants in pollen | |
| 002 | 0,070.7 | From 10% to 90% pollen shed | |
| | | From 50% silk to harvest at 25% moisture | |

3. PLANT:

| | | Standard Deviation | Sample Size |
|---|---|---|---|
| 0,189.3 cm | Plant Height (to tassel tip) | 19.86 | 15 |
| 0,055.3 cm | Ear Height (to base of top ear node) | 7.23 | 15 |
| 0,012.7 cm | Length of Top Ear Internode | 0.50 | 15 |
| 0.0 | Average Number of Tillers | 0.03 | 3 |
| 0.9 | Average Number of Ears per Stalk | 0.07 | 3 |
| 2.0 | Anthocyanin of Brace Roots: 1 = Absent 2 = Faint 3 = Moderate 4 = Dark | | |

4: LEAF:

| | | Standard Deviation | Sample Size |
|---|---|---|---|
| 009.5 cm | Width of Ear Node Leaf | 0.31 | 15 |
| 082.3 cm | Length of Ear Node Leaf | 0.61 | 15 |
| 05.9 | Number of leaves above top ear | 0.58 | 15 |
| 017.6 | Degrees Leaf Angle (measure from 2nd leaf above ear at anthesis to stalk above leaf) | 2.12 | 15 |
| 03 | Leaf Color   Dark Green   (Munsell code) | 5GY34 | |
| 1.0 | Leaf Sheath Pubescence (Rate on scale from 1 = none to 9 = like peach fuzz) | | |
| | Marginal Waves (Rate on scale from 1 = none to 9 = many) | | |
| | Longitudinal Creases (Rate on scale from 1 = none to 9 = many) | | |

5. TASSEL:

| | | Standard Deviation | Sample Size |
|---|---|---|---|
| 01.3 | Number of Primary Lateral Branches | 0.81 | 15 |
| 016.7 | Branch Angle from Central Spike | 3.83 | 15 |
| 58.7 cm | Tassel Length (from top leaf collar to tassel tip) | 3.38 | 15 |
| 3.7 | Pollen Shed (rate on scale from 0 = male sterile to 9 = heavy shed) | | |
| 01 | Anther Color   Light Green   (Munsell code) | 5GY88 | |
| 01 | Glume Color   Light Green   (Munsell code) | 5GY58 | |
| 1.0 | Bar Glumes (Glume Bands): 1 = Absent 2 = Present | | |
| 22 cm | Peduncle Length (cm. from top leaf to basal branches) | | |

6a. EAR (Unhusked Data):

| 1 | Silk Color (3 days after emergence) | Light Green | (Munsell code) | 2.5GY96 |
|---|---|---|---|---|
| 1 | Fresh Husk Color (25 days after 50% silking) | Light Green | (Munsell code) | 5GY66 |
| 21 | Dry Husk Color (65 days after 50% silking) | Buff | (Munsell code) | 10YR92 |

TABLE 1-continued

VARIETY DESCRIPTION INFORMATION
VARIETY = PH8V0

| | | | | |
|---|---|---|---|---|
| 1 | Position of Ear at Dry Husk Stage: 1 = Upright 2 = Horizontal 3 = Pendant | | | Upright |
| 4 | Husk Tightness (Rate of Scale from 1 = very loose to 9 = very tight) | | | |
| 2 | Husk Extension (at harvest): 1 = Short (ears exposed) 2 = Medium (<8 cm) | | | |
| | 3 = Long (8–10 cm beyond ear tip) 4 = Very Long (>10 cm) | | | Medium |
| 6b. EAR (Husked Ear Data): | | Standard Deviation | Sample Size | |
| 19 cm | Ear Length | 1.15 | 15 | |
| 42 mm | Ear Diameter at mid-point | 1.15 | 15 | |
| 138 gm | Ear weight | 15.04 | 15 | |
| 17 | Number of Kernel Rows | 1.53 | 15 | |
| 2 | Kernel Rows: 1 = Indistinct 2 = Distinct | | | Distinct |
| 1 | Row Alignment: 1 = Straight 2 = Slightly Curved 3 = Spiral | | | Straight |
| 11 cm | Shank Length | 2.31 | 15 | |
| 2 | Ear Taper: 1 = Slight 2 = Average 3 = Extreme | | | Average |
| 7. KERNEL (Dried): | | Standard Deviation | Sample Size | |
| 11 mm | Kernel Length | 0.58 | 15 | |
| 8 mm | Kernel Width | 0.00 | 15 | |
| 5 mm | Kernel Thickness | 0.00 | 15 | |
| 46 | % Round Kernels (Shape Grade) | 4.58 | 3 | |
| 1 | Aleurone Color Pattern: 1 = Homozygous 2 = Segregating | | | Homozygous |
| 7 | Aluerone Color Yellow | (Munsell code) | 10YR14 | |
| 10 | Hard Endosperm Color Pink-Orange | (Munsell code) | 10YR712 | |
| 5 | Endosperm Type: Waxy Starch | | | |
| | 1 = Sweet (Su1) 2 = Extra Sweet (sh2) 3 = Normal Starch | | | |
| | 4 = High Amylose Starch 5 = Waxy Starch 6 = High Protein | | | |
| | 7 = High Lysine 8 = Super Sweet (se) 9 = High Oil | | | |
| | 10 = Other_____ | | | |
| 27 gm | Weight per 100 Kernels (unsized sample) | 1.00 | 3 | |
| 8. COB: | | Standard Deviation | Sample Size | |
| 23 mm | Cob Diameter at mid-point | 1.00 | 15 | |
| 14 | Cob Color Red | (Munsell code) | 2.5R38 | |

9. DISEASE RESISTANCE (Rate from 1 (most susceptible) to 9 (most resistant); leave blank if not tested; leave Race or Strain Options blank if polygenic):
    A. Leaf Blights, Wilts, and Local Infection Diseases
        Anthracnose Leaf Blight (*Colletotrichum graminicola*)
        Common Rust (*Puccinia sorghi*)
        Common Smut (*Ustilago maydis*)
        Eyespot (*Kabatiella zeae*)
        Goss's Wilt (*Clavibacter michiganense* spp. *nebraskense*)
      4 Gray Leaf Spot (*Cercospora zeae-maydis*)
        Helminthosporium Leaf Spot (*Bipolaris zeicola*) Race_____
      6 Northern Leaf Blight (*Exserohilum turcicum*) Race_____
      5 Southern Leaf Blight (*Bipolaris maydis*) Race_____
        Southern Rust (*Puccinia polysora*)
      6 Stewart's Wilt (*Erwinia stewartii*)
        Other (Specify)_____
    B. Systemic Diseases
        Corn Lethal Necrosis (MCMV and MDMV)
        Head Smut (*Sphacelotheca reiliana*)
        Maize Chlorotic Dwarf Virus (MDV)
        Maize Chlorotic Mottle Virus (MCMV)
        Maize Dwarf Mosaic Virus (MDMV)
        Sorghum Downy Mildew of Corn (*Peronosclerospora sorghi*)
        Other (Specify)_____
    C. Stalk Rots
      4 Anthracnose Stalk Rot (*Colletotrichum graminicola*)
        Diplodia Stalk Rot (*Stenocarpella maydis*)
        Fusarium Stalk Rot (*Fusarium moniliforme*)
        Gibberella Stalk Rot (*Gibberella zeae*)
        Other (Specify)_____
    D. Ear and kernel Rots
        Aspergillus Ear and Kernel Rot (*Aspergillus flavus*)
      3 Diplodia Ear Rot (*Stenocarpella maydis*)
      3 Fusarium Ear and Kernel Rot (*Fusarium moniliforme*)
        Gibberella Ear Rot (*Gibberella zeae*)
        Other (Specify)_____

10. INSECT RESISTANCE (Rate from 1 (most susceptible) to 9 (most resistant);
        (leave blank if not tested):
        Banks grass Mite (*Oligonychus pratensis*)
        Corn Worm (*Helicoverpa zea*)
         Leaf Feeding
         Silk Feeding
          mg larval wt.
        Ear Damage

TABLE 1-continued

VARIETY DESCRIPTION INFORMATION
VARIETY = PH8V0

|   |   |
|---|---|
|   | Corn Leaf Aphid (*Rhopalosiphum maidis*) |
|   | Corn Sap Beetle (*Carpophilus dimidiatus*) |
|   | European Corn Borer (*Ostrinia nubilalis*) |
| 4 | 1st Generation (Typically Whorl Leaf Feeding) |
|   | 2nd Generation (Typically Leaf Sheath-Collar Feeding) |
|   | Stalk Tunneling |
|   | cm tunneled/plant |
|   | Fall Armyworm (*Spodoptera fruqiperda*) |
|   | Leaf Feeding |
|   | Silk Feeding |
|   | mg larval wt. |
|   | Maize Weevil (*Sitophilus zeamaize* |
|   | Northern Rootworm (*Diabrotica barberi*) |
|   | Southern Rootworm (*Diabrotica undecimpunctata*) |
|   | Southwestern Corn Borer (*Diatreaea grandiosella*) |
|   | Leaf Feeding |
|   | Stalk Tunneling |
|   | cm tunneled/plant |
|   | Two-spotted Spider Mite (*Tetranychus urticae*) |
|   | Western Rootworm (*Diabrotica virgifrea virgifera*) |
|   | Other (Specify)_____ |
| 11. AGRONOMIC TRAITS: | |
| 4 | Staygreen (at 65 days after anthesis) (Rate on a scale from 1 = worst to 9 = excellent) |
| 0.0 | % Dropped Ears (at 65 days after anthesis) |
|   | % Pre-anthesis Brittle Snapping |
|   | % Pre-anthesis Root Lodging |
| 12.4 | Post-anthesis Root Lodging (at 65 days after anthesis) |
| 4,804 | Kg/ha Yield (at 12–13% grain moisture) |

*In interpreting the foregoing color designations, reference may be made to the Munsell Glossy Book of Color, a standard color reference.

FURTHER EMBODIMENTS OF THE INVENTION

This invention also is directed to methods for producing a maize plant by crossing a first parent maize plant with a second parent maize plant wherein either the first or second parent maize plant is an inbred maize plant of the line PH8V0. Further, both first and second parent maize plants can come from the inbred maize line PH8V0. Still further, this invention also is directed to methods for producing an inbred maize line PH8V0 -derived maize plant by crossing inbred maize line PH8V0 with a second maize plant and growing the progeny seed, and repeating the crossing and growing steps with the inbred maize line PH8V0 -derived plant from 0 to 5 times. Thus, any such methods using the inbred maize line PH8V0 are part of this invention: selfing, backcrosses, hybrid production, crosses to populations, and the like. All plants produced using inbred maize line PH8V0 as a parent are within the scope of this invention, including plants derived from inbred maize line PH8V0. Advantageously, the inbred maize line is used in crosses with other, different, maize inbreds to produce first generation ($F_1$) maize hybrid seeds and plants with superior characteristics.

A further embodiment of the invention is a single gene conversion or introgression of the maize plant disclosed herein in which the gene or genes of interest (encoding the desired trait) are introduced through traditional (non-transformation) breeding techniques, such as backcrossing (Hallauer et al, 1988). One or more genes may be introduced using these techniques. Desired traits transferred through this process include, but are not limited to, waxy starch, nutritional enhancements, industrial enhancements, disease resistance, insect resistance, herbicide resistance and yield enhancements. The gene of interest is transferred from the donor parent to the recurrent parent, in this case, the maize plant disclosed herein. These single gene traits may result from either the transfer of a dominant allele or a recessive allele. Selection of progeny containing the trait of interest is done by direct selection for a trait associated with a dominant allele. Selection of progeny for a trait that is transferred via a recessive allele, such as the waxy starch characteristic, requires growing and selfing the first backcross to determine which plants carry the recessive alleles. Recessive traits may require additional progeny testing in successive backcross generations to determine the presence of the gene of interest.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which maize plants can be regenerated, plant calli, plant clumps, and plant cells that are intact in plants or parts of plants, such as embryos, pollen, ovules, seeds, flowers, kernels, ears, cobs, leaves, husks, stalks, roots, root tips, anthers, silk and the like.

Duncan, Williams, Zehr, and Widholm, Planta (1985) 165:322–332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in *Plant Cell Reports* (1988), 7:262–265 reports several media additions that enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter,* 60:64–65 (1986), refers to somatic embryogenesis from glume callus cultures and B. V. Conger, et al., *Plant Cell Reports,* 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," Maize *for Biological Research* (Plant Molecular Biology Association, Charlottesville, Va. 1982, at 367–372) and in Duncan, et al., "The Production of Callus Capable of Plant Regeneration from Immature Embryos of Numerous *Zea Mays Genotypes*," 165 *Planta* 322–332 (1985). Thus, another aspect of this invention is to provide cells which upon growth and differentiation produce maize plants having the physiological and morphological characteristics of inbred line PH8V0.

The utility of inbred maize line PH8V0 also extends to crosses with other species. Commonly, suitable species will be of the family Graminaceae, and especially of the genera *Zea, Tripsacum, Coix, Schlerachne, Polytoca, Chionachne*, and *Trilobachne*, of the tribe Maydeae. Potentially suitable for crosses with PH8V0 may be the various varieties of grain sorghum, *Sorghum bicolor* (L.) Moench.

Transformation of Maize

With the advent of molecular biological techniques that have allowed the isolation and characterization of genes that encode specific protein products, scientists in the field of plant biology developed a strong interest in engineering the genome of plants to contain and express foreign genes, or additional, or modifed versions of native or endogenous genes (perhaps driven by different promoters) in order to alter the traits of a plant in a specific manner. Such foreign, additional and/or modified genes are referred to herein collectively as "transgenes". Over the last fifteen to twenty years several methods for producing transgenic plants have been developed, and the present invention, in particular embodiments, also relates to transformed versions of the claimed inbred maize line PH8V0.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used, alone or in combination with other plasmids, to provide transformed maize plants, using transformation methods as described below to incorporate transgenes into the genetic material of the maize plant(s).

Expression Vectors For Maize Transformation

Marker Genes

Expression vectors include at least one genetic marker, operably linked to a regulatory element (a promoter, for example) that allows transformed cells containing the marker to be either recovered by negative selection, i.e. inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Nati. Acad. Sci. U.S.A.*, 80: 4803 (1983). Another commonly used selectable marker gene is the hygromycin phosphotransferase gene which confers resistance to the antibiotic hygromycin. Vanden Elzen et al., *Plant Mol. Biol*, 5: 299 (1985).

Additional selectable marker genes of bacterial origin that confer resistance to antibiotics include gentamycin acetyl transferase, streptomycin phosphotransferase, aminoglycoside- 3'-adenyl transferase, the bleomycin resistance determinant. Hayford et al., *Plant Physiol.* 86: 1216 (1988), Jones et al, *Mol. Gen. Genet.*, 210: 86 (1987), Svab et al., *Plant Mol. Biol.* 14: 197 (1990), Hille et al., *Plant Mol. Biol.* 7:171 (1986). Other selectable marker genes confer resistance to herbicides such as glyphosate, glufosinate or broxynil. Comai et al, *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5-eno/pyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., *EMBO J.* 3: 1681 (1984). Another approach to the identification of relatively rare transformation events has been use of a gene that encodes a dominant constitutive regulator of the Zea mays anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green™, p. 1–4 (1993) and Naleway et al., *J. Cell Biol.*1 15: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al, *Science* 263: 802 (1994). GFP and mutants of GFP may be used as screenable markers.

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in maize. Optionally, the inducible promoter is operably linked to a nucleotide sequence encoding a signal sequence which is operably linked to a gene for expression in maize. With an inducible promoter the rate of transcription increases in response to an inducing agent.

Any inducible promoter can be used in the instant invention. See Ward et al. *Plant Mol. Biol.*22: 361–366 (1993). Exemplary inducible promoters include, but are not limited to, that from the ACEI system which responds to copper (Mett et al PNAS 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et al, *Mol. Gen. Genet.* 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Nati. Acad. Sci. U.S.A.* 88: 0421 (1991).

B. Constitutive Promoters

A constitutive promoter is operably linked to a gene for expression in maize or the constitutive promoter is operably linked to a nucleotide sequence encoding a signal sequence which is operably linked to a gene for expression in maize.

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)); ubiquitin (Christensen et al., *Plant Mol. Biol* 12: 619–632 (1989) and Christensen et al, *Plant Mol. Biol.* 18: 675–689 (1992)): pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.* 231: 276–285 (1992) and Atanassova et al., *Plant Journal*2 (3): 291–300 (1992)).

The ALS promoter, a Xbal/Ncol fragment 5' to the Brassica napus ALS3 structural gene (or a nucleotide sequence that has substantial sequence similarity to said Xbal/Ncol fragment), represents a particularly useful constitutive promoter. See PCT application W096/30530.

C. Tissue-specific or Tissue-Preferred Promoters

A tissue-specific promoter is operably linked to a gene for expression in maize. Optionally, the tissue-specific promoter is operably linked to a nucleotide sequence encoding a signal sequence which is operably linked to a gene for expression in maize. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23: 476–482 (1983) and Sengupta-Gopalan et al., *Proc. Natl. Acad. Sci. USA* 82: 3320–3324 (1985)); a leaf-specific and light-induced promoter such as that from cab or rubisco (Simpson et al, *EMBO J.* 4(11): 2723–2729 (1985) and Timko et al, *Nature* 318: 579–582 (1985)); an anther-specific promoter such as that from LAT52 (Twell et al., *Mol. Gen. Genet.* 217: 240–245 (1989)); a pollen-specific promoter such as that from Zm13 (Guerrero et al., *Mol. Gen. Genet.*224: 161–168 (1993)) or a microspore-preferred promoter such as that from apg (Twell et al., *Sex. Plant Reprod.* 6: 217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Becker et al, *Plant Mol. Biol.*20: 49 (1992), Close, P. S., Master's Thesis, Iowa State University (1993), Knox, C., et al., "Structure and Organization of Two Divergent Alpha-Amylase Genes From Barley", *Plant Mol.Biol.* 9: 3–17 (1987), Lerner et al., *Plant Physiol.*91: 124–129 (1989), Fontes et al., *Plant Cell* 3: 483–496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-lzquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is maize. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, *METHODS IN PLANT MOLECULAR BIOLOGY AND BIOTECHNOLOGY* 269–284 (CRC Press, Boca Raton,1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below.

1. Genes that Confer Resistance to Pests or Disease and that Encode (A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266: 789 (1994) (cloning of the tomato Cf-9 gene for resistance to *Cladosporium fulvum*); Martin et al., *Science* 262: 1432 (1993) (tomato Pto gene for resistance to Pseudomonas syringae pv. tomato encodes a protein kinase); Mindrinos et al., *Cell* 78: 1089 (1994) (Arabidopsis RSP2 gene for resistance to *Pseudomonas syringae*).

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(C) A lectin. See, for example, the disclosure by Van Damme et al., *Plant Molec. Biol.* 24: 25 (1994), who disclose the nucleotide sequences of several Clivia miniata mannose-binding lectin genes.

(D) A vitamin-binding protein such as avidin. See PCT application US93/06487 the contents of which are hereby incorporated by. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor 1), and Sumitani et al., *Biosci. Biotech. Biochem.* 57: 1243 (1993) (nucleotide sequence of *Streptomyces nitrosporeus* α-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in Diploptera puntata). See also U.S. pat. No. 5,266,317 to Tomalski et al., who disclose genes encoding insect-specific, paralytic neurotoxins.

(H) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.*23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4–2 polyubiquitin gene.

(K) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(L) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(M) A membrane permease, a channel former or a channel blocker. For example, see the disclosure by Jaynes et al.,

*Plant Sci.* 89: 43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al, *Ann. Rev. Phytopathol* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf Taylor et al., Abstract #497, *SEVENTH INT'L SYMPOSIUM ON MOLECULAR PLANT-MICROBE INTERACTIONS* (Edinburgh, Scotland, 1994) (enzymatic inactivation in transgenic tobacco via production of single-chain antibody fragments).

(P) A virus-specific antibody. See, for example, Tavladoraki et al., *Nature* 366: 469 (1993), who show that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10: 1436 (1992). The cloning and characterization of a gene which encodes a bean endopolygalacturonase-inhibiting protein is described by Toubart et al, *Plant J.* 2: 367 (1992).

(R) A developmental-arrestive protein produced in nature by a plant For example, Logemann et al, *Bio/Technology* 10: 305 (1992), have shown that transgenic plants expressing the barley ribosome-inactivating gene have an increased resistance to fungal disease.

2. Genes that Confer Resistance to a Herbicide, for Example (A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl.Genet.* 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor Appl Genet.* 83: 435 (1992).

(C) A herbicide that inhibits photosynthesis, such as a triazine (psbA and gs+genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J* 285: 173 (1992).

3. Genes that Confer or Contribute to a Value-Added Trait, such as (A) Modified fatty acid metabolism, for example, by transforming a plant with an antisense gene of stearoyl-ACP desaturase to increase stearic acid content of the plant. See Knultzon et al, *Proc. Natl. Acad. Sci. USA* 89: 2624 (1992).

(B) Decreased phytate content (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. BacterioL* 170: 810 (1988) (nucleotide sequence of *streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et al, *Plant Molec. Biol.* 21: 515 (1993) (nucleotide sequences of tomato invertase genes), Søgaard et al, *J. Biol. Chem.* 268: 22480 (1993) (site-directed mutagenesis of barley α-amylase gene), and Fisher et al., *Plant Physiol.* 102: 1045 (1993) (maize endosperm starch branching enzyme 11).

Methods for Maize Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al, *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant. Sci.*10: 1 (1991). Descriptions of Agrobacterium vector systems and methods for Agrobacterium-mediated gene transfer are provided by Gruber et al, supra, Miki et al., supra, and Moloney et al., *Plant Cell Reports* 8: 238 (1989). See also, U.S. Pat. No. 5,591,616, issued Jan. 7, 1997.

B. Direct Gene Transfer

Despite the fact the host range for Agrobacterium-mediated transformation is broad, some major cereal crop species and gymnosperms have generally been recalcitrant to this mode of gene transfer, even though some success has recently been achieved in rice and maize. Hiei et al., *The Plant Journal* 6: 271–282 (1994); U.S. Pat. No. 5,591,616, issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 $\mu$m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559–563 (1988), Sanford, J. C., *Physiol Plant* 79: 206 (1990), Klein et al, *Biotechnology* 10: 268 (1992). In maize, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al, *EMBO J.,* 4: 2731 (1985), Christou et al, *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.*199: 161 (1985) and Draper et al., *Plant Cell Physiol.*23: 451 (1982). Electroporation of protoplasts and whole cells and tissues have also been described. Donn et al., In Abstracts of VIIth International Congress on Plant Cell and Tissue Culture IAPTC, A2–38, p 53 (1990); D'Halluin et al., *Plant Cell* 4: 1495–1505 (1992) and Spencer et al., *Plant Mol. Biol.* 24: 51–61 (1994).

Following transformation of maize target tissues, expression of the above-described selectable marker genes allows for preferential selection of transformed cells, tissues and/or plants, using regeneration and selection methods now well known in the art. For example, transformed maize immature embryos.

The foregoing methods for transformation would typically be used for producing transgenic inbred lines. Transgenic inbred lines could then be crossed, with another (non-transformed or transformed) inbred line, in order to produce a transgenic hybrid maize plant. Alternatively, a genetic trait which has been engineered into a particular maize line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid maize plant containing a foreign gene in its genome into a line or lines which do not contain that gene. As used herein, "crossing" can refer to a simple X by Y cross, or the process of backcrossing, depending on the context.

Industrial Applicability

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of inbred maize line PH8V0, the plant produced from the inbred seed, the hybrid maize plant produced from the crossing of the inbred, hybrid seed, and various parts of the hybrid maize plant and transgenic versions of the foregoing, can be utilized for human food, livestock feed, and as a raw material in industry.

Performance Examples of PH8V0

In the examples that follow, the traits and characteristics of inbred maize line PH8V0 are given as a line. The data collected on inbred maize line PH8V0 is presented for the key characteristics and traits.

Inbred Comparisons

The results in Table 2A compare inbred PH8V0 to inbred PHJ8R. The results show inbred PH8V0 demonstrates significantly lower harvest moisture than inbred PHJ8R. The PH8V0 inbred flowers (GDU SHD and GDU SLK) significantly earlier than the PHJ8R inbred. The PH8V0 inbred presents a significantly shorter plant with significantly lower ear placement than the PHJ8R inbred. Inbred PH8V0 shows above average cold test results.

The results in Table 2B compare inbred PH8V0 to inbred PH5P7. The results show inbred PH8V0 demonstrates significantly lower harvest moisture than inbred PH5P7. The PH8V0 inbred flowers (GDU SHD and GDU SLK) significantly earlier than the PH5P7 inbred. The PH8V0 inbred presents a significantly shorter plant with significantly lower ear placement than the PH5P7 inbred. Inbred PH8V0 shows above average cold test results.

The results in Table 2C compare inbred PH8V0 to inbred PH44A. The results show inbred PH8V0 demonstrates significantly lower yields with significantly higher harvest moisture than inbred PH44A. The PH8V0 inbred flowers (GDU SHD and GDU SLK) significantly later than the PH44A inbred. Inbred PH8V0 shows above average cold test results.

Inbred by Tester Comparisons

The results in Table 3 compare the inbred PH8V0 and inbred PHJ8R, when each inbred is crossed to the same tester lines. The PH8V0 hybrid demonstrates good yields with significantly lower harvest moisture than the PHJ8R hybrid. The PH8V0 presents a shorter than average plant with significantly lower ear placement than the PHJ8R hybrid. The PH8V0 hybrids shows above average staygreen scores and above average resistance to stalk lodging.

Hybrid Comparisons

The results in Table 4A compare inbred PH8V0 crossed to inbred PH7M8 and inbred PH4F0 crossed to PH9E4. The results show the PH8V0/PH7M8 hybrid to demonstrate significantly lower yields with significantly lower test weight of grain than the PH4F0/PH9E4 hybrid. The PH8V0/PH7M8 hybrid presents a significantly shorter plant than the PH4F0/PH9E4 hybrid.

The results in Table 4B compare inbred PH8V0 crossed to inbred PH7M8 and inbred PHJ8R crossed to PH7M8. The results show the PH8V0/PH7M8 hybrid to demonstrate significantly lower yields but with significantly lower harvest moisture than the PHJ8R/PH7M8 hybrid. The PH8V0/PH7M8 hybrid presents a shorter than average plant with significantly lower ear placement than the PHJ8R/PH7M8 hybrid. The PH8V0/PH7M8 hybrid shows above average staygreen scores and above average resistance to stalk lodging. The PH8V0/PH7M8 hybrid exhibits significantly lower amounts of oil from the grain and significantly higher amounts of starch from the grain than the PHJ8R/PH7M8 hybrid.

The results in Table 4C compare inbred PH8V0 crossed to inbred PH7M8 and inbred PH44A crossed to PH24E. The results show the PH8V0/PH7M8 hybrid to demonstrate above average yields but with significantly higher harvest moisture than the PH44A/PH24E hybrid. The PH8V0/PH7M8 hybrid shows significantly better early season growth than the PH44APH24E hybrid. The PH8V0/PH7M8 hybrid presents a shorter than average plant. The PH8V0/PH7M8 hybrid shows above average and significantly higher staygreen scores than the PH44A/PH24E hybrid. The PH8V0/PH7M8 hybrid exhibits above average and significantly better resistance to stalk lodging than the PH44APH24E hybrid.

The results in Table 4D compare inbred PH8V0 crossed to inbred PH7M8 and inbred PH5P7 crossed to PH2K1. The results show the PH8V0/PH7M8 hybrid to demonstrate above average yields with significantly lower harvest moisture and significantly higher test weight of grain than the PH5P7/PH2K1 hybrid. The PH8V0/PH7M8 hybrid flowers (GDU SHD and GDU SLK) significantly earlier than the PH5P7/PH2K1 hybrid. The PH8V0/PH7M8 hybrid presents a significantly shorter plant with significantly lower ear placement than the PH5P7/PH2K1 hybrid. The PH8V0/PH7M8 hybrid shows above average and significantly higher staygreen scores than the PH5P7/PH2K1 hybrid. The PH8V0/PH7M8 hybrid exhibits above average and significantly better resistance to stalk lodging than the PH5P7/PH2K1 hybrid.

TABLE 2A

PAIRED INBRED COMPARISON REPORT
VARIETY #1 = PH8V0
VARIETY #2 = PHJ8R

| | | BU ACR ABS | BU ACR % MN | MST ABS | TST WT ABS | EGR WTH ABS | EST CNT ABS | TIL LER ABS | GDU SHD ABS | GDU SLK ABS |
|---|---|---|---|---|---|---|---|---|---|---|
| TOTAL SUM | 1 | 79.0 | 94 | 18.0 | 54.8 | 5.3 | 26.0 | 2.5 | 139.0 | 139.1 |
| | 2 | 93.5 | 111 | 21.9 | 55.6 | 5.7 | 26.8 | 7.8 | 142.2 | 144.2 |
| | LOCS | 12 | 12 | 13 | 2 | 21 | 35 | 21 | 49 | 49 |
| | REPS | 12 | 12 | 13 | 2 | 21 | 42 | 21 | 49 | 49 |
| | DIFF | 14.5 | 18 | 3.9 | 0.8 | 0.4 | 0.7 | 5.3 | 3.2 | 5.1 |
| | PR > T | .010+ | .007# | .001# | .681 | .189 | .138 | .226 | .000# | .000# |

| | | TAS BLS ABS | TAS SZ ABS | PLT HT ABS | EAR HT ABS | RT LDG ABS | STA GRN ABS | STK LDG ABS | BRT STK ABS | SCT GRN ABS |
|---|---|---|---|---|---|---|---|---|---|---|
| TOTAL SUM | 1 | 2.0 | 2.2 | 80.1 | 30.2 | 90.9 | 4.4 | 96.4 | 85.6 | 5.8 |
| | 2 | 4.5 | 4.5 | 86.3 | 38.2 | 75.5 | 5.4 | 100.0 | 84.9 | 7.6 |
| | LOCS | 2 | 28 | 33 | 11 | 4 | 10 | 1 | 3 | 10 |
| | REPS | 2 | 28 | 33 | 11 | 4 | 10 | 1 | 3 | 10 |
| | DIFF | 2.5 | 2.3 | 6.2 | 8.0 | 15.4 | 1.0 | 3.6 | 0.6 | 1.8 |
| | PR > T | .126 | .000# | .000# | .000# | .391 | .096* | | .965 | .001# |

| | | EAR MLD ABS | BAR PLT ABS | GLF SPT ABS | NLF BLT ABS | SLF BLT ABS | STW WLT ABS | ANT ROT ABS | HD SMT ABS | FUS ERS ABS |
|---|---|---|---|---|---|---|---|---|---|---|
| TOTAL SUM | 1 | 4.9 | 93.7 | 3.6 | 5.0 | 6.0 | 5.5 | 3.3 | 100.0 | 3.0 |
| | 2 | 6.9 | 97.0 | 3.9 | 6.0 | 6.0 | 5.3 | 4.5 | 100.0 | 4.5 |
| | LOCS | 8 | 28 | 9 | 1 | 1 | 2 | 2 | 1 | 4 |
| | REPS | 8 | 28 | 13 | 2 | 2 | 3 | 4 | 1 | 4 |
| | DIFF | 2.0 | 3.4 | 0.3 | 1.0 | 0.0 | 0.3 | 1.3 | 0.0 | 1.5 |
| | PR > T | .063* | .009# | .550 | | | .874 | .126 | | .339 |

TABLE 2A-continued

PAIRED INBRED COMPARISON REPORT
VARIETY #1 = PH8V0
VARIETY #2 = PHJ8R

|  |  | DIP ERS ABS | ECB 1LF ABS | CLD TST ABS | CLD TST % MN | KSZ DCD ABS |
|---|---|---|---|---|---|---|
|  | TOTAL SUM 1 | 3.0 | 4.0 | 87.7 | 105 | 4.4 |
|  | 2 | 2.0 | 5.3 | 89.7 | 107 | 1.8 |
|  | LOCS | 1 | 3 | 6 | 6 | 5 |
|  | REPS | 1 | 3 | 6 | 6 | 5 |
|  | DIFF | 1.0 | 1.3 | 2.0 | 2 | 2.6 |
|  | PR > T |  | .270 | .611 | .646 | .090* |

*= 10% SIG
+= 5% SIG
= 1% SIG

TABLE 2B

PAIRED INBRED COMPARISON REPORT
VARIETY #1 = PH8V0
VARIETY #2 = PH5P7

|  |  | BU ACR ABS | BU ACR % MN | MST ABS | TST WT ABS | EGR WTH ABS | EST CNT ABS | TIL LER ABS | GDU SHD ABS | GDU SLK ABS |
|---|---|---|---|---|---|---|---|---|---|---|
| TOTAL SUM | 1 | 75.5 | 94 | 18.6 | 53.5 | 5.2 | 30.6 | 2.1 | 139.5 | 139.8 |
|  | 2 | 89.2 | 113 | 22.5 | 55.5 | 5.0 | 31.6 | 1.2 | 145.5 | 146.5 |
|  | LOCS | 20 | 20 | 23 | 3 | 21 | 47 | 29 | 58 | 58 |
|  | REPS | 25 | 25 | 28 | 4 | 22 | 65 | 30 | 58 | 58 |
|  | DIFF | 13.7 | 18 | 3.9 | 1.9 | 0.2 | 1.0 | 0.9 | 6.0 | 6.7 |
|  | PR > T | .004# | .005# | .000# | .119 | .358 | .076* | .118 | .000# | .000# |

|  |  | TAS BLS ABS | TAS SZ ABS | PLT HT ABS | EAR HT ABS | RT LDG ABS | STA GRN ABS | STK LDG ABS | BRT STK ABS | SCT GRN ABS |
|---|---|---|---|---|---|---|---|---|---|---|
| TOTAL SUM | 1 | 2.0 | 2.2 | 79.9 | 31.1 | 89.9 | 4.8 | 91.4 | 84.9 | 5.7 |
|  | 2 | 4.0 | 2.9 | 83.6 | 37.3 | 97.8 | 5.2 | 97.6 | 92.9 | 7.0 |
|  | LOCS | 2 | 34 | 41 | 16 | 5 | 12 | 3 | 5 | 12 |
|  | REPS | 2 | 34 | 42 | 17 | 5 | 13 | 4 | 7 | 12 |
|  | DIFF | 2.0 | 0.7 | 3.7 | 6.3 | 7.9 | 0.5 | 6.2 | 7.9 | 1.3 |
|  | PR > T | .000# | .000# | .003# | .000# | .237 | .347 | .045+ | .197 | .010+ |

|  |  | EAR MLD ABS | BAR PLT ABS | DRP EAR ABS | GLF SPT ABS | STW WLT ABS | FUS ERS ABS | CLD TST ABS | CLD TST % MN | KSZ DCD ABS |
|---|---|---|---|---|---|---|---|---|---|---|
| TOTAL SUM | 1 | 5.3 | 94.0 | 100.0 | 4.7 | 5.0 | 2.3 | 80.3 | 101 | 4.5 |
|  | 2 | 7.7 | 97.3 | 100.0 | 4.3 | 6.0 | 5.8 | 80.8 | 102 | 2.3 |
|  | LOCS | 9 | 36 | 2 | 6 | 1 | 4 | 8 | 8 | 8 |
|  | REPS | 9 | 38 | 3 | 6 | 1 | 4 | 8 | 8 | 8 |
|  | DIFF | 2.3 | 3.3 | 0.0 | 0.3 | 1.0 | 3.5 | 0.5 | 1 | 2.3 |
|  | PR > T | .011+ | .010+ | .999 | .363 |  | .035+ | .906 | .882 | .122 |

*= 10% SIG
+= 5% SIG
= 1% SIG

TABLE 2C

PAIRED INBRED COMPARISON REPORT
VARIETY #1 = PH8V0
VARIETY #2 = PH44A

|  |  | BU ACR ABS | BU ACR % MN | MST ABS | TST WT ABS | EGR WTH ABS | EST CNT ABS | TIL LER ABS | GDU SHD ABS | GDU SLK ABS |
|---|---|---|---|---|---|---|---|---|---|---|
| TOTAL SUM | 1 | 76.6 | 97 | 18.2 | 55.2 | 5.3 | 32.4 | 1.9 | 139.3 | 139.7 |
|  | 2 | 87.0 | 111 | 16.6 | 54.8 | 5.2 | 32.8 | 0.9 | 138.4 | 138.1 |
|  | LOCS | 40 | 40 | 44 | 9 | 31 | 59 | 34 | 62 | 62 |
|  | REPS | 45 | 45 | 49 | 10 | 32 | 70 | 35 | 62 | 62 |

TABLE 2C-continued

PAIRED INBRED COMPARISON REPORT
VARIETY #1 = PH8V0
VARIETY #2 = PH44A

|  | | | | | | | | | |
|---|---|---|---|---|---|---|---|---|---|
| DIFF | 10.4 | 14 | 1.7 | 0.3 | 0.1 | 0.4 | 1.0 | 0.9 | 1.6 |
| PR > T | .003# | .003# | .000# | .714 | .598 | .460 | .234 | .027+ | .000# |

|  | | TAS BLS ABS | TAS SZ ABS | PLT HT ABS | EAR HT ABS | RT LDG ABS | STA GRN ABS | STK LDG ABS | BRT STK ABS | SCT GRN ABS |
|---|---|---|---|---|---|---|---|---|---|---|
| TOTAL SUM | 1 | 2.0 | 2.2 | 80.1 | 31.6 | 87.6 | 4.2 | 94.8 | 92.7 | 5.7 |
|  | 2 | 1.5 | 2.0 | 79.1 | 30.9 | 90.3 | 4.1 | 91.7 | 95.7 | 6.8 |
|  | LOCS | 2 | 36 | 43 | 18 | 9 | 15 | 5 | 7 | 12 |
|  | REPS | 2 | 36 | 44 | 19 | 9 | 17 | 6 | 8 | 12 |
|  | DIFF | 0.5 | 0.3 | 1.0 | 0.8 | 2.7 | 0.1 | 3.2 | 3.0 | 1.1 |
|  | PR > T | .500 | .027+ | .144 | .471 | .349 | .805 | .437 | .496 | .047+ |

|  | | EAR MLD ABS | BAR PLT ABS | DRP EAR ABS | GLF SPT ABS | NLF BLT ABS | SLF BLT ABS | STW WLT ABS | ANT ROT ABS | HD SMT ABS |
|---|---|---|---|---|---|---|---|---|---|---|
| TOTAL SUM | 1 | 5.3 | 94.0 | 100.0 | 4.0 | 6.3 | 4.3 | 5.0 | 4.0 | 28.6 |
|  | 2 | 6.4 | 96.2 | 100.0 | 4.1 | 6.8 | 4.8 | 5.0 | 3.3 | 70.8 |
|  | LOCS | 9 | 39 | 3 | 13 | 2 | 2 | 1 | 2 | 1 |
|  | REPS | 9 | 41 | 4 | 20 | 4 | 4 | 1 | 4 | 2 |
|  | DIFF | 1.1 | 2.2 | 0.0 | 0.2 | 0.5 | 0.5 | 0.0 | 0.8 | 42.2 |
|  | PR > T | .179 | .031+ | .999 | .515 | .500 | .500 |  | .205 |  |

|  | | FUS ERS ABS | ECB 1LF ABS | CLD TST ABS | CLD TST % MN | KSZ DCD ABS |
|---|---|---|---|---|---|---|
| TOTAL SUM | 1 | 2.7 | 4.0 | 85.1 | 101 | 4.5 |
|  | 2 | 2.8 | 4.7 | 87.6 | 105 | 6.1 |
|  | LOCS | 5 | 3 | 17 | 17 | 16 |
|  | REPS | 6 | 3 | 17 | 17 | 16 |
|  | DIFF | 0.1 | 0.7 | 2.5 | 4 | 1.6 |
|  | PR > T | .704 | .184 | .435 | .397 | .048+ |

\*= 10% SIG
+= 5% SIG
= 1% SIG

TABLE 3

Average Inbred By Tester Performance Comparing PH8V0 To PHJ8R Crossed To The Same Inbred Testers And Grown In The Same Experiments.

|  | | PRM ABS | BU ACR ABS | BU ACR % MN | PRM SHD ABS | MST % MN | EGR WTH % MN | GDU SHD % MN | GDU SLK % MN | STK CNT % MN | PLT HT % MN |
|---|---|---|---|---|---|---|---|---|---|---|---|
| TOTAL SUM | REPS | 3 | 212 | 212 | 3 | 214 | 28 | 28 | 28 | 304 | 74 |
|  | LOCS | 3 | 106 | 106 | 3 | 107 | 14 | 14 | 14 | 152 | 37 |
|  | PH8V0 | 107 | 180 | 100 | 107 | 98 | 98 | 100 | 100 | 99 | 97 |
|  | PHJ8R | 111 | 186 | 103 | 107 | 106 | 100 | 100 | 100 | 99 | 96 |
|  | DIFF | 3 | 5 | 3 | 0 | 8 | 2 | 1 | 0 | 0 | 1 |
|  | PR > T | 0.00 | 0.01 | 0.01 | 0.99 | 0.00 | 0.72 | 0.32 | 0.99 | 0.99 | 0.11 |

|  | | EAR HT % MN | RT LDG % MN | STA GRN % MN | STK LDG % MN | BRT STK % MN | STW WLT ABS | ANT ROT ABS | FUS ERS ABS | GIB ERS ABS | DIP ERS ABS |
|---|---|---|---|---|---|---|---|---|---|---|---|
| TOTAL SUM | REPS | 74 | 8 | 66 | 104 | 4 | 4 | 6 | 2 | 4 | 2 |
|  | LOCS | 37 | 4 | 33 | 52 | 2 | 2 | 3 | 1 | 2 | 1 |
|  | PH8V0 | 96 | 101 | 113 | 105 | 96 | 7 | 6 | 5 | 7 | 4 |
|  | PHJ8R | 102 | 99 | 125 | 104 | 104 | 7 | 5 | 6 | 7 | 4 |
|  | DIFF | 5 | 2 | 12 | 1 | 8 | 0 | 0 | 1 | 0 | 1 |
|  | PR > T | 0.00 | 0.19 | 0.02 | 0.68 | 0.11 | 0.99 | 0.99 |  | 0.99 |  |

|  | | EYE SPT ABS | ECB 1LF ABS | ECB 2SC ABS | DRP EAR % MN | GLF SPT ABS | NLF BLT ABS |
|---|---|---|---|---|---|---|---|
| TOTAL SUN | REPS | 2 | 6 | 2 | 24 | 14 | 4 |
|  | LOCS | 1 | 3 | 1 | 12 | 7 | 2 |

TABLE 3-continued

Average Inbred By Tester Performance Comparing PH8V0 To PHJ8R Crossed
To The Same Inbred Testers And Grown In The Same Experiments.

|  |  |  |  |  |  |  |  |
|---|---|---|---|---|---|---|---|
| PH8V0 | 7 | 6 | 5 | 100 | 5 | 7 |
| PHJ8R | 6 | 5 | 6 | 100 | 5 | 7 |
| DIFF | 1 | 1 | 1 | 0 | 0 | 0 |
| PR > T |  | 0.23 |  | 0.99 | 0.99 | 0.99 |

*PR > T values are valid only for comparisons with Locs >= 10.

TABLE 4A

INBREDS IN HYBRID COMBINATION REPORT
VARIETY #1 = PH8V0/PH7M8
VARIETY #2 = PH4F0/PH9E4

|  |  | PRM ABS | BU ACR ABS | BU ACR % MN | TST WT % MN | MST ABS | STK CNT % MN | PLT HT % MN | STA GRN % MN |
|---|---|---|---|---|---|---|---|---|---|
| TOTAL SUM | 1 | 109 | 179.6 | 93 | 88 | 58.6 | 101 | 95 | 97 |
|  | 2 | 114 | 206.7 | 107 | 109 | 57.8 | 102 | 103 | 107 |
|  | LOCS | 4 | 28 | 28 | 28 | 24 | 27 | 8 | 8 |
|  | REPS | 4 | 28 | 28 | 28 | 24 | 27 | 8 | 8 |
|  | DIFF | 5 | 27.1 | 14 | 21 | 0.7 | 1 | 8 | 11 |
|  | PR > T | .002# | .000# | .000# | .000# | .225 | .477 | .003# | .494 |

*= 10% SIG
+= 5% SIG
= 1% SIG

TABLE 4B

INBREDS IN HYBRID COMBINATION REPORT
VARIETY #1 = PH8V0/PH7M8
VARIETY #2 = PHJ8R/PH7M8

|  |  | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|---|
| TOTAL SUM | 1 | 108 | 107 | 183.1 | 100 | 101 | 56.5 | 98 | 113 | 100 |
|  | 2 | 111 | 107 | 189.9 | 104 | 109 | 55.9 | 99 | 111 | 100 |
|  | LOCS | 3 | 1 | 85 | 85 | 86 | 58 | 17 | 1 | 16 |
|  | REPS | 3 | 1 | 85 | 85 | 86 | 58 | 17 | 1 | 18 |
|  | DIFF | 3 | 0 | 6.8 | 4 | 8 | 0.6 | 1 | 2 | 0 |
|  | PR > T | .024+ |  | .001# | .001# | .000# | .025+ | .880 |  | .999 |

|  |  | GDU SLK % MN | STK CNT % MN | PLT HT % MN | EAR HT % MN | RT LDG % MN | STA GRN % MN | STK LDG % MN | BRT STK % MN | DRP EAR % MN |
|---|---|---|---|---|---|---|---|---|---|---|
| TOTAL SUM | 1 | 100 | 99 | 98 | 96 | 101 | 123 | 104 | 96 | 99 |
|  | 2 | 100 | 100 | 97 | 104 | 99 | 132 | 104 | 104 | 100 |
|  | LOCS | 16 | 114 | 28 | 24 | 4 | 25 | 47 | 2 | 12 |
|  | REPS | 18 | 141 | 28 | 24 | 4 | 25 | 47 | 2 | 13 |
|  | DIFF | 0 | 1 | 1 | 7 | 2 | 9 | 0 | 9 | 0 |
|  | PR > T | .999 | .084* | .128 | .001# | .193 | .080* | .999 | .116 | .999 |

|  |  | GLF SPT ABS | NLF BLT ABS | STW WLT ABS | ANT ROT ABS | FUS ERS ABS | GIB ERS ABS | DIP ERS ABS | EYE SPT ABS | ECB 1LF ABS |
|---|---|---|---|---|---|---|---|---|---|---|
| TOTAL SUM | 1 | 4.9 | 7.3 | 6.5 | 5.5 | 4.3 | 7.0 | 4.0 | 6.5 | 5.8 |
|  | 2 | 4.6 | 7.0 | 6.8 | 5.3 | 5.3 | 7.0 | 3.5 | 6.0 | 5.3 |
|  | LOCS | 7 | 2 | 2 | 3 | 2 | 2 | 1 | 1 | 3 |
|  | REPS | 10 | 3 | 4 | 6 | 3 | 3 | 2 | 2 | 5 |
|  | DIFF | 0.3 | 0.3 | 0.3 | 0.2 | 1.0 | 0.0 | 0.5 | 0.5 | 0.5 |
|  | PR > T | .522 | .500 | .500 | .826 | .000# | .999 |  |  | .225 |

|  |  | ECB 2SC ABS | HSK CVR ABS | HSK CVR % MN | OIL T ABS | PRO T ABS | STR T ABS |
|---|---|---|---|---|---|---|---|
| TOTAL SUM | 1 | 4.5 | 5.7 | 97 | 4.0 | 8.9 | 71.3 |
|  | 2 | 5.5 | 5.7 | 98 | 4.7 | 9.4 | 70.1 |

TABLE 4B-continued

INBREDS IN HYBRID COMBINATION REPORT
VARIETY #1 = PH8V0/PH7M8
VARIETY #2 = PHJ8R/PH7M8

| | | | | LOCS | 1 | 3 | 3 | 12 | 12 | 12 |
|---|---|---|---|---|---|---|---|---|---|---|
| | | | | REPS | 2 | 3 | 3 | 12 | 12 | 12 |
| | | | | DIFF | 1.0 | 0.0 | 1 | 0.7 | 0.5 | 1.2 |
| | | | | PR > T | | .999 | .932 | .000# | .059* | .000# |

*= 10% SIG
+= 5% SIG
= 1% SIG

TABLE 4C

INBREDS IN HYBRID COMBINATION REPORT
VARIETY #1 = PH8V0/PH7M8
VARIETY #2 = PH44A/PH24E

| | | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|---|
| TOTAL SUM | 1 | 107 | 107 | 178.5 | 103 | 101 | 55.9 | 95 | 97 | 100 |
| | 2 | 106 | 107 | 179.1 | 103 | 95 | 56.1 | 87 | 99 | 100 |
| | LOCS | 3 | 3 | 166 | 166 | 168 | 88 | 38 | 28 | 44 |
| | REPS | 3 | 3 | 168 | 168 | 170 | 90 | 39 | 28 | 47 |
| | DIFF | 2 | 1 | 0.7 | 0 | 5 | 0.3 | 8 | 2 | 1 |
| | PR > T | .053* | .106 | .637 | .999 | .000# | .042+ | .008# | .279 | .128 |

| | | GDU SLK % MN | STK CNT % MN | PLT HT % MN | EAR HT % MN | RT LDG % MN | STA GRN % MN | STK LDG % MN | BRT STK % MN | DRP EAR % MN |
|---|---|---|---|---|---|---|---|---|---|---|
| TOTAL SUM | 1 | 99 | 98 | 98 | 96 | 85 | 131 | 106 | 104 | 100 |
| | 2 | 100 | 101 | 99 | 97 | 81 | 113 | 103 | 105 | 99 |
| | LOCS | 28 | 234 | 64 | 64 | 36 | 45 | 86 | 36 | 30 |
| | REPS | 31 | 286 | 67 | 67 | 36 | 45 | 88 | 37 | 31 |
| | DIFF | 0 | 3 | 1 | 1 | 3 | 18 | 4 | 1 | 1 |
| | PR > T | .999 | .000# | .062* | .289 | .447 | .000# | .001# | .306 | .313 |

| | | GLF SPT ABS | NLF BLT ABS | GOS WLT ABS | STW WLT ABS | ANT ROT ABS | FUS ERS ABS | GIB ERS ABS | DIP ERS ABS | EYE SPT ABS |
|---|---|---|---|---|---|---|---|---|---|---|
| TOTAL SUM | 1 | 4.6 | 6.7 | 7.0 | 6.5 | 5.7 | 4.2 | 6.8 | 4.0 | 6.5 |
| | 2 | 4.5 | 6.8 | 8.0 | 6.4 | 4.3 | 3.7 | 6.3 | 3.5 | 6.0 |
| | LOCS | 17 | 5 | 1 | 6 | 7 | 3 | 4 | 1 | 1 |
| | REPS | 23 | 8 | 2 | 8 | 12 | 4 | 6 | 2 | 2 |
| | DIFF | 0.1 | 0.1 | 1.0 | 0.1 | 1.4 | 0.5 | 0.5 | 0.5 | 0.5 |
| | PR > T | .614 | .838 | | .363 | .085* | .225 | .495 | | |

| | | ECB 1LF ABS | HSK CVR ABS | HSK CVR % MN | OIL T ABS | PRO T ABS | STR T ABS |
|---|---|---|---|---|---|---|---|
| TOTAL SUM | 1 | 5.0 | 6.1 | 102 | 4.2 | 9.4 | 71.0 |
| | 2 | 4.0 | 5.7 | 95 | 4.0 | 9.5 | 71.5 |
| | LOCS | 1 | 7 | 7 | 19 | 19 | 19 |
| | REPS | 1 | 7 | 7 | 19 | 19 | 19 |
| | DIFF | 1.0 | 0.4 | 7 | 0.1 | 0.1 | 0.5 |
| | PR > T | | .289 | .341 | .034+ | .529 | .040+ |

*= 10% SIG
+= 5% SIG
= 1% SIG

TABLE 4D

INBREDS IN HYBRID COMBINATION REPORT
VARIETY #1 = PH8V0/PH7M8
VARIETY #2 = PH5P7/PH2K1

| | | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|---|
| TOTAL SUM | 1 | 109 | 107 | 174.2 | 102 | 98 | 56.5 | 93 | 97 | 99 |

TABLE 4D-continued

INBREDS IN HYBRID COMBINATION REPORT
VARIETY #1 = PH8V0/PH7M8
VARIETY #2 = PH5P7/PH2K1

|  | 2 | 110 | 108 | 177.5 | 104 | 103 | 56.0 | 96 | 98 | 101 |
|---|---|---|---|---|---|---|---|---|---|---|
|  | LOCS | 8 | 3 | 184 | 184 | 186 | 105 | 29 | 28 | 44 |
|  | REPS | 8 | 3 | 186 | 186 | 188 | 107 | 30 | 28 | 47 |
|  | DIFF | 1 | 1 | 3.3 | 3 | 5 | 0.5 | 3 | 2 | 2 |
|  | PR > T | .000# | .122 | .032+ | .007# | .000# | .006# | .504 | .463 | .000# |

|  |  | GDU SLK % MN | STK CNT % MN | PLT HT % MN | EAR HT % MN | RT LDG % MN | STA GRN % MN | STK LDG % MN | BRT STK % MN | DRP EAR % MN |
|---|---|---|---|---|---|---|---|---|---|---|
| TOTAL SUM | 1 | 99 | 98 | 97 | 96 | 87 | 128 | 107 | 104 | 100 |
|  | 2 | 101 | 101 | 100 | 105 | 107 | 116 | 97 | 102 | 101 |
|  | LOCS | 27 | 250 | 65 | 57 | 41 | 49 | 77 | 36 | 30 |
|  | REPS | 30 | 303 | 68 | 60 | 41 | 49 | 79 | 37 | 31 |
|  | DIFF | 2 | 3 | 2 | 9 | 20 | 12 | 9 | 2 | 1 |
|  | PR > T | .000# | .000# | .000# | .000# | .002# | .022+ | .000# | .258 | .092* |

|  |  | GLF SPT ABS | NLF BLT ABS | GOS WLT ABS | STW WLT ABS | ANT ROT ABS | FUS ERS ABS | GIB ERS ABS | DIP ERS ABS | EYE SPT ABS |
|---|---|---|---|---|---|---|---|---|---|---|
| TOTAL SUM | 1 | 4.6 | 6.6 | 7.0 | 6.5 | 5.7 | 4.3 | 6.8 | 4.0 | 6.5 |
|  | 2 | 5.1 | 5.8 | 8.0 | 5.8 | 3.3 | 4.3 | 6.5 | 4.5 | 7.0 |
|  | LOCS | 17 | 4 | 1 | 6 | 7 | 2 | 4 | 1 | 1 |
|  | REPS | 23 | 7 | 2 | 8 | 12 | 3 | 6 | 2 | 2 |
|  | DIFF | 0.5 | 0.9 | 1.0 | 0.8 | 2.4 | 0.0 | 0.3 | 0.5 | 0.5 |
|  | PR > T | .038+ | .069* |  | .091* | .022+ | .999 | .839 |  |  |

|  |  | CDM RST ABS | ECB 1LF ABS | ECB 2SC ABS | HSK CVR ABS | HSK CVR % MN | OIL T ABS | PRO T ABS | STR T ABS |
|---|---|---|---|---|---|---|---|---|---|
| TOTAL SUM | 1 | 6.0 | 5.8 | 4.0 | 6.1 | 102 | 4.1 | 9.5 | 71.0 |
|  | 2 | 5.5 | 4.5 | 5.0 | 7.3 | 123 | 4.2 | 9.5 | 71.3 |
|  | LOCS | 2 | 3 | 1 | 7 | 7 | 18 | 18 | 18 |
|  | REPS | 2 | 5 | 1 | 7 | 7 | 18 | 18 | 18 |
|  | DIFF | 0.5 | 1.3 | 1.0 | 1.1 | 21 | 0.0 | 0.0 | 0.3 |
|  | PR > T | .795 | .057* |  | .231 | .232 | .999 | .999 | .020+ |

*= 10% SIG
+= 5% SIG
= 1% SIG

Deposits

Applicants have made a deposit of at least 2500 seeds of Inbred Maize Line PH8V0 with the American Type Culture Collection (ATCC), Manassas, VA 20110 USA, ATCC Deposit No. PTA-3508. The seeds deposited with the ATCC on Jul. 11, 2001 were taken from the deposit maintained by Pioneer Hi-Bred International, Inc., 800 Capital Square, 400 Locust Street, Des Moines, Iowa 50309–2340 since prior to the filing date of this application. This deposit of the Inbred Maize Line PH8V0 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of their rights granted under this patent or under the Plant Variety Protection Act (7 USC 2321 et seq.). U.S. Plant Variety Protection of Inbred Maize Line PH8V0 has been applied for under Application No. 200000205.

The foregoing invention has been described in detail by way of illustration and example for purposes of clarity and understanding. However, it will be obvious that certain changes and modifications such as single gene conversions and mutations, somoclonal variants, variant individuals selected from large populations of the plants of the instant inbred and the like may be practiced within the scope of the invention, as limited only by the scope of the appended claims.

What is claimed is:

1. Seed of maize inbred line designated PH8V0, representative seed of said line having been deposited under ATCC Accession No. PTA-3508.

2. A maize plant, or parts thereof, produced by growing the seed of claim 1.

3. The maize plant of claim 2, wherein said plant is male sterile.

4. A tissue culture of regenerable cells from the plant of claim 2.

5. A tissue culture according to claim 4, the cells or protoplasts being from a tissue selected from the group consisting of leaves, pollen, embryos, roots, root tips, anthers, silks, flowers, kernels, ears, cobs, husks, and stalks.

6. A maize plant regenerated from the tissue culture of claim 4, capable of expressing all the morphological and physiological characteristics of inbred line PH8V0, representative seed of which have been deposited under ATCC Accession No. PTA-3508.

7. A method for producing a first generation ($F_1$) hybrid maize seed comprising crossing the plant of claim 2 with a different inbred parent maize plant and harvesting the resultant first generation ($F_1$) hybrid maize seed.

8. The method of claim 7 wherein the inbred maize plant of claim 2 is the female or male parent.

9. An $F_1$ hybrid seed produced by crossing the inbred maize plant according to claim 2 with another, different maize plant.

10. An $F_1$ hybrid plant, or parts thereof, grown from the seed of claim 9.

11. The maize plant, or parts thereof, of claim 2, wherein the plant or parts thereof have been transformed so that its genetic material contains one or more transgenes operably linked to one or more regulatory elements.

12. A method for producing a maize plant that contains in its genetic material one or more transgenes, comprising crossing the maize plant of claim 11 with either a second plant of another maize line, or a non-transformed maize plant of the line PH8V0, so that the genetic material of the progeny that result from the cross contains the transgene(s) operably linked to a regulatory element.

13. Maize plants, or parts thereof, produced by the method of claim 12.

14. A maize plant, or parts thereof, wherein at least one ancestor of said maize plant is the maize plant of claim 2, said maize plant expressing a combination of at least two PH8V0 traits selected from the group consisting of: a relative maturity of approximately 106 based on the Comparative Relative Maturity Rating System for harvest moisture of grain, high yields, good cold test scores, waxy starch grain, good resistance to stalk lodging, good staygreen, low harvest moisture, below average plant height, and adapted to the Central Corn Belt region of the United States.

15. A method for developing a maize plant in a maize plant breeding program using plant breeding techniques, which include employing a maize plant, or its parts, as a source of plant breeding material, comprising: obtaining the maize plant, or its parts, of claim 2 as a source of said breeding material.

16. The maize plant breeding program of claim 15 wherein plant breeding techniques are selected from the group consisting of: recurrent selection, backcrossing, pedigree breeding, restriction fragment length polymorphism enhanced selection, genetic marker enhanced selection, and transformation.

17. A maize plant, or parts thereof, produced by the method of claim 15.

18. The maize plants, or parts thereof, of claim 2, further comprising one or more single gene conversions.

19. The single gene conversion(s) of claim 18, wherein the gene is a dominant allele.

20. The single gene conversion(s) of claim 18, wherein the gene is a recessive allele.

21. A maize plant, or parts thereof, having all the physiological and morphological characteristics of inbred line PH8V0, representative seed of said line having been deposited under ATCC Accession No. PTA-3508.

22. The maize plant of claim 21, wherein said plant is male sterile.

23. A tissue culture of regenerable cells from the plant of claim 21.

24. A tissue culture according to claim 23, the cells or protoplasts being from a tissue selected from the group consisting of leaves, pollen, embryos, roots, root tips, anthers, silks, flowers, kernels, ears, cobs, husks, and stalks.

25. A maize plant regenerated from the tissue culture of claim 23, capable of expressing all the morphological and physiological characteristics of inbred line PH8V0, representative seed of which have been deposited under ATCC Accession No. PTA-3508.

26. A method for producing a first generation ($F_1$) hybrid maize seed comprising crossing the plant of claim 21 with a different inbred parent maize plant and harvesting the resultant first generation ($F_1$) hybrid maize seed.

27. The method of claim 26 wherein the inbred maize plant of claim 21 is the female or male parent.

28. An $F_1$ hybrid seed produced by crossing the inbred maize plant according to claim 21 with another, different maize plant.

29. An $F_1$ hybrid plant, or parts thereof, grown from the seed of claim 28.

30. The maize plant, or parts thereof, of claim 21, wherein the plant or parts thereof have been transformed so that its genetic material contains one or more transgenes operably linked to one or more regulatory elements.

31. A method for producing a maize plant that contains in its genetic material one or more transgenes, comprising crossing the maize plant of claim 30 with either a second plant of another maize line, or a non-transformed maize plant of the line PH8V0, so that the genetic material of the progeny that result from the cross contains the transgene(s) operably linked to a regulatory element.

32. Maize plants, or parts thereof, produced by the method of claim 31.

33. A maize plant, or parts thereof, wherein at least one ancestor of said maize plant is the maize plant of claim 21, said maize plant expressing a combination of at least two PH8V0 traits selected from the group consisting of: a relative maturity of approximately 106 based on the Comparative Relative Maturity Rating System for harvest moisture of grain, high yields, good cold test scores, waxy starch grain, good resistance to stalk lodging, good staygreen, low harvest moisture, below average plant height, and adapted to the Central Corn Belt region of the United States.

34. A method for developing a maize plant in a maize plant breeding program using plant breeding techniques, which include employing a maize plant, or its parts, as a source of plant breeding material, comprising: obtaining the maize plant, or its parts, of claim 21 as a source of said breeding material.

35. The maize plant breeding program of claim 34 wherein plant breeding techniques are selected from the group consisting of: recurrent selection, backcrossing, pedigree breeding, restriction fragment length polymorphism enhanced selection, genetic marker enhanced selection, and transformation.

36. A maize plant, or parts thereof, produced by the method of claim 34.

37. A process for producing inbred PH8V0, representative seed of which have been deposited under ATCC Accession No. PTA-3508, comprising:
   (a) planting a collection of seed comprising seed of a hybrid, one of whose parents is inbred PH8V0 said collection also comprising seed of said inbred;
   (b) growing plants from said collection of seed;
   (c) identifying inbred parent plants;
   (d) selecting said inbred parent plant;
   (e) controlling pollination through selfing, which preserves the homozygosity of said inbred parent plant; and
   (f) collecting morphological and/or physiological data so that said inbred parent may be identified as inbred PH8V0.

38. The process of claim 37 wherein step (c) comprises identifying plants with decreased vigor.

39. The process of claim 37 wherein step (c) comprises identifying seeds or plants with homozygous genotype.

40. A method for producing a PH8V0-derived maize plant, comprising:
(a) crossing inbred maize line PH8V0, representative seed of said line having been deposited under ATCC Accession No. PTA-3508, with a second maize plant to yield progeny maize seed;
(b) growing said progeny maize seed, under plant growth conditions, to yield said PH8V0-derived maize plant.

41. A PH8V0-derived maize plant, or parts thereof, produced by the method of claim 40, said PH8V0-derived maize plant expressing a combination of at east two PH8V0 traits selected from the group consisting of: a relative maturity of approximately 106 based on the Comparative Relative Maturity Rating System for harvest moisture of grain, high yields, good cold test scores, waxy starch grain, good resistance to stalk lodging, good staygreen, low harvest moisture, below average plant height, and adapted to the Central Corn Belt region of the United States.

42. The method of claim 40, further comprising:
(c) crossing said PH8V0-derived maize plant with itself or another maize plant to yield additional PH8V0-derived progeny maize seed;
(d) growing said progeny maize seed of step (c) under plant growth conditions, to yield additional PH8V0-derived maize plants;
(e) repeating the crossing and growing steps of (c) and (d) from 0 to 5 times to generate further PH8V0-derived maize plants.

43. A further derived maize plant, or parts thereof, produced by the method of claim 42.

44. The method of claim 40, still further comprising utilizing plant tissue culture methods to derive progeny of said PH8V0-derived maize plant.

45. A PH8V0-derived maize plant, or parts thereof, produced by the method of claim 44, said PH8V0-derived maize plant expressing a combination of at least two PH8V0 traits selected from the group consisting of: a relative maturity of approximately 106 based on the Comparative Relative Maturity Rating System for harvest moisture of grain, high yields, good cold test scores, waxy starch grain, good resistance to stalk lodging, good staygreen, low harvest moisture, below average plant height, and adapted to the Central Corn Belt region of the United States.

46. The further PH8V0-derived maize plant, or parts thereof, of claim 43, wherein said further PH8V0-derived maize plant, or parts thereof, express a combination of at least two PH8V0 traits selected from the group consisting of: a relative maturity of approximately 106 based on the Comparative Relative Maturity Rating System for harvest moisture of grain, high yields, good cold test scores, waxy starch grain, good resistance to stalk lodging, good staygreen, low harvest moisture, below average plant height, and adapted to the Central Corn Belt region of the United States.

47. The maize plants, or parts thereof, of claim 21, further comprising one or more single gene conversions.

48. The single gene conversion(s) of claim 47, wherein the gene is a dominant allele.

49. The single gene conversion(s) of claim 47, wherein the gene is a recessive allele.

* * * * *